US012308122B2

(12) United States Patent
Boussios et al.

(10) Patent No.: US 12,308,122 B2
(45) Date of Patent: *May 20, 2025

(54) APPLYING PREDICTIVE MODELS TO DATA REPRESENTING A HISTORY OF EVENTS

(71) Applicant: OM1, Inc., Boston, MA (US)

(72) Inventors: Constantinos Ioannis Boussios, Chelsea, MA (US); Francis Thomas O'Donovan, Arlington, MA (US); Richard Gliklich, Weston, MA (US)

(73) Assignee: OM1, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/596,720

(22) Filed: Mar. 6, 2024

(65) Prior Publication Data
US 2024/0290491 A1 Aug. 29, 2024

Related U.S. Application Data

(63) Continuation of application No. 16/386,123, filed on Apr. 16, 2019, now Pat. No. 11,967,428.
(Continued)

(51) Int. Cl.
*G16H 50/20* (2018.01)
*G06F 16/2458* (2019.01)
(Continued)

(52) U.S. Cl.
CPC ......... *G16H 50/20* (2018.01); *G06F 16/2462* (2019.01); *G06F 16/2477* (2019.01);
(Continued)

(58) Field of Classification Search
CPC ........ G16H 50/20; G16H 50/70; G06N 20/00; G06F 16/2477; G06F 16/2462; G06F 18/2148; G06F 18/217
See application file for complete search history.

(56) References Cited

U.S. PATENT DOCUMENTS

| 5,486,999 A | 1/1996 | Mebane |
| 5,508,912 A | 4/1996 | Schneiderman |

(Continued)

FOREIGN PATENT DOCUMENTS

| EP | 2614480 A2 | 7/2013 |
| WO | 0057310 A1 | 9/2000 |

(Continued)

OTHER PUBLICATIONS

Voshaar, et al., "Calibration of the PROMIS Physical Function Item Bank in Dutch Patients with Rheumatoid Arthritis", PLOS ONE, vol. 9, Issue 3, Mar. 2014, pp. 1-11.
(Continued)

*Primary Examiner* — Debbie M Le
*Assistant Examiner* — Huen Wong
(74) *Attorney, Agent, or Firm* — Outside General Counsel LLP; Peter Gordon

(57) ABSTRACT

A predictive model can be applied to data representing a history of events for an entity to compute a value indicative of an outcome related to a reference time for that entity. The effect of an event from an entity's history of events on an outcome for the entity at a reference time can vary based on the type of event and relative time of that event with respect to the reference time. The effect of an event from an entity's history of events on an outcome for the entity also can vary due to other characteristics of the entity in combination with the event. These effects are captured as weights. For an entity, functions of sets of events from the history of events are computed for the entity and a set of weights for events. The computed results are inputs to the predictive model.

30 Claims, 9 Drawing Sheets

Related U.S. Application Data

(60) Provisional application No. 62/658,868, filed on Apr. 17, 2018.

(51) Int. Cl.
*G06F 18/21* (2023.01)
*G06F 18/214* (2023.01)
*G06N 20/00* (2019.01)
*G16H 50/70* (2018.01)

(52) U.S. Cl.
CPC ........ *G06F 18/2148* (2023.01); *G06F 18/217* (2023.01); *G06N 20/00* (2019.01); *G16H 50/70* (2018.01)

(56) References Cited

U.S. PATENT DOCUMENTS

| | | | |
|---|---|---|---|
| 5,619,421 A | 4/1997 | Venkataraman et al. | |
| 5,961,332 A | 10/1999 | Joao | |
| 6,101,511 A | 8/2000 | Derose et al. | |
| 6,317,731 B1 | 11/2001 | Luciano | |
| 6,524,241 B2* | 2/2003 | Iliff | G16H 70/60 |
| | | | 128/920 |
| 6,687,685 B1 | 2/2004 | Sadeghi et al. | |
| 7,076,437 B1 | 7/2006 | Levy | |
| 7,194,301 B2 | 3/2007 | Jenkins et al. | |
| 7,433,519 B2 | 10/2008 | Rynderman | |
| 7,739,126 B1 | 6/2010 | Cave et al. | |
| 7,809,660 B2 | 10/2010 | Friedlander et al. | |
| 7,916,363 B2 | 3/2011 | Rynderman | |
| 7,930,262 B2 | 4/2011 | Friedlander et al. | |
| 7,949,620 B2 | 5/2011 | Otte et al. | |
| 8,090,590 B2 | 1/2012 | Fotsch et al. | |
| 8,140,541 B2 | 3/2012 | Koss | |
| 8,154,776 B2 | 4/2012 | Rynderman | |
| 8,165,973 B2 | 4/2012 | Alexe et al. | |
| 8,311,849 B2 | 11/2012 | Soto et al. | |
| 8,335,698 B2 | 12/2012 | Angell et al. | |
| 8,392,215 B2 | 3/2013 | Tawil | |
| 8,538,773 B2 | 9/2013 | Eddy et al. | |
| 8,560,281 B2 | 10/2013 | Soto et al. | |
| 8,583,586 B2 | 11/2013 | Ebadollahi et al. | |
| 8,930,223 B2 | 1/2015 | Friedlander et al. | |
| 9,514,416 B2 | 12/2016 | Lee et al. | |
| 9,646,271 B2 | 5/2017 | Friedlander et al. | |
| 9,690,844 B2 | 6/2017 | Mukherjee et al. | |
| 10,061,812 B2 | 8/2018 | Marshall et al. | |
| 10,282,512 B2 | 5/2019 | Bennett et al. | |
| 10,311,363 B1 | 6/2019 | Florissi et al. | |
| 10,311,975 B2 | 6/2019 | Young et al. | |
| 10,706,329 B2 | 7/2020 | Anushiravani et al. | |
| 10,731,223 B2 | 8/2020 | Kennedy et al. | |
| 10,731,233 B2 | 8/2020 | Yamada et al. | |
| 11,257,574 B1 | 2/2022 | Boussios et al. | |
| 11,527,326 B2* | 12/2022 | McNair | G16H 10/60 |
| 11,594,310 B1 | 2/2023 | Bradley et al. | |
| 11,594,311 B1 | 2/2023 | Bradley et al. | |
| 11,862,346 B1 | 1/2024 | Boussios et al. | |
| 11,967,428 B1 | 4/2024 | Boussios et al. | |
| 12,057,204 B2 | 8/2024 | Bradley et al. | |
| 12,142,355 B2 | 11/2024 | Bradley et al. | |
| 2003/0014284 A1 | 1/2003 | Jones | |
| 2004/0122706 A1 | 6/2004 | Walker et al. | |
| 2004/0122707 A1 | 6/2004 | Sabol et al. | |
| 2004/0243362 A1 | 12/2004 | Liebman | |
| 2006/0058384 A1 | 3/2006 | Hogg | |
| 2006/0129427 A1* | 6/2006 | Wennberg | G06Q 10/00 |
| | | | 703/2 |
| 2006/0129428 A1* | 6/2006 | Wennberg | G16H 50/50 |
| | | | 703/2 |
| 2006/0173663 A1* | 8/2006 | Langheier | G16H 50/20 |
| | | | 703/11 |
| 2007/0021979 A1* | 1/2007 | Cosentino | A61B 5/318 |
| | | | 600/300 |
| 2007/0172907 A1* | 7/2007 | Volker | G16B 40/00 |
| | | | 435/15 |
| 2007/0255113 A1* | 11/2007 | Grimes | G16H 50/20 |
| | | | 600/300 |
| 2008/0171916 A1 | 7/2008 | Feder et al. | |
| 2008/0208813 A1 | 8/2008 | Friedlander et al. | |
| 2008/0235049 A1* | 9/2008 | Morita | G16H 50/20 |
| | | | 705/2 |
| 2008/0294459 A1 | 11/2008 | Angell et al. | |
| 2009/0119337 A1 | 5/2009 | Biedermann | |
| 2009/0164237 A1 | 6/2009 | Hunt et al. | |
| 2009/0259494 A1 | 10/2009 | Feder et al. | |
| 2009/0287503 A1 | 11/2009 | Angell et al. | |
| 2010/0021956 A1* | 1/2010 | Shearer | G01N 33/92 |
| | | | 435/29 |
| 2010/0191088 A1 | 7/2010 | Anderson et al. | |
| 2010/0240035 A1* | 9/2010 | Jablons | C12Q 1/6886 |
| | | | 435/6.14 |
| 2010/0324927 A1 | 12/2010 | Tinsley | |
| 2011/0010328 A1 | 1/2011 | Patel et al. | |
| 2011/0071363 A1 | 3/2011 | Montijo et al. | |
| 2011/0106558 A1 | 5/2011 | Solito et al. | |
| 2011/0125680 A1 | 5/2011 | Bosworth et al. | |
| 2011/0177956 A1 | 7/2011 | Korenberg | |
| 2011/0288877 A1 | 11/2011 | Ofek et al. | |
| 2012/0065987 A1 | 3/2012 | Farooq et al. | |
| 2012/0084064 A1 | 4/2012 | Dzenis et al. | |
| 2012/0110016 A1 | 5/2012 | Phillips | |
| 2012/0179478 A1 | 7/2012 | Ross | |
| 2012/0191640 A1 | 7/2012 | Ebadollahi et al. | |
| 2012/0215560 A1 | 8/2012 | Ofek et al. | |
| 2012/0254098 A1 | 10/2012 | Flinn et al. | |
| 2012/0296675 A1 | 11/2012 | Silverman | |
| 2013/0185231 A1 | 7/2013 | Baras et al. | |
| 2014/0006447 A1 | 1/2014 | Friedlander et al. | |
| 2014/0074510 A1* | 3/2014 | McClung | G16H 50/30 |
| | | | 705/3 |
| 2014/0081898 A1 | 3/2014 | Saigal et al. | |
| 2014/0095204 A1 | 4/2014 | Fung et al. | |
| 2014/0108044 A1 | 4/2014 | Reddy et al. | |
| 2014/0164022 A1 | 6/2014 | Reed et al. | |
| 2014/0249834 A1 | 9/2014 | D'Souza et al. | |
| 2014/0350954 A1 | 11/2014 | Ellis et al. | |
| 2015/0106109 A1 | 4/2015 | Crowley et al. | |
| 2015/0106115 A1 | 4/2015 | Hu et al. | |
| 2015/0235001 A1 | 8/2015 | Fouts | |
| 2015/0339442 A1 | 11/2015 | Oleynik | |
| 2015/0347599 A1 | 12/2015 | McMains et al. | |
| 2016/0004840 A1 | 1/2016 | Rust et al. | |
| 2016/0012202 A1 | 1/2016 | Hu et al. | |
| 2016/0015347 A1 | 1/2016 | Bregman-Amitai et al. | |
| 2016/0029919 A1 | 2/2016 | Hebert et al. | |
| 2016/0078183 A1 | 3/2016 | Trygstad et al. | |
| 2016/0120481 A1 | 5/2016 | Li et al. | |
| 2016/0188814 A1 | 6/2016 | Raghavan et al. | |
| 2016/0188834 A1 | 6/2016 | Erdmann et al. | |
| 2016/0196394 A1 | 7/2016 | Chanthasiriphan et al. | |
| 2016/0235373 A1 | 8/2016 | Sharma et al. | |
| 2016/0283679 A1 | 9/2016 | Hu et al. | |
| 2016/0283686 A1 | 9/2016 | Hu et al. | |
| 2016/0354039 A1 | 12/2016 | Soto et al. | |
| 2017/0046602 A1 | 2/2017 | Hu et al. | |
| 2017/0061093 A1* | 3/2017 | Amarasingham | G16H 10/60 |
| 2017/0124263 A1 | 5/2017 | Crafts et al. | |
| 2017/0124279 A1 | 5/2017 | Rothman | |
| 2017/0147777 A1 | 5/2017 | Kim et al. | |
| 2017/0235887 A1 | 8/2017 | Cox et al. | |
| 2017/0262609 A1 | 9/2017 | Perlroth et al. | |
| 2017/0323075 A1 | 11/2017 | Krause et al. | |
| 2018/0268937 A1 | 9/2018 | Spetzler et al. | |
| 2018/0330805 A1 | 11/2018 | Cheung et al. | |
| 2018/0336319 A1 | 11/2018 | Itu et al. | |
| 2019/0079938 A1 | 3/2019 | Agrawal et al. | |
| 2019/0244714 A1* | 8/2019 | Morra | G06F 17/15 |
| 2020/0411164 A1 | 12/2020 | Donner | |
| 2021/0098090 A1 | 4/2021 | Thomas et al. | |
| 2022/0148695 A1 | 5/2022 | Boussios et al. | |
| 2023/0197223 A1 | 6/2023 | Bradley et al. | |

(56) References Cited

U.S. PATENT DOCUMENTS

| | | | |
|---|---|---|---|
| 2023/0197224 | A1 | 6/2023 | Bradley et al. |
| 2024/0096500 | A1 | 3/2024 | Boussios et al. |
| 2024/0153647 | A1 | 5/2024 | Boussios et al. |

FOREIGN PATENT DOCUMENTS

| | | | |
|---|---|---|---|
| WO | 0209004 | A1 | 1/2002 |
| WO | 0209580 | A1 | 2/2002 |
| WO | 03/104939 | A2 | 12/2003 |
| WO | 2006086181 | A1 | 8/2006 |
| WO | 2007050147 | A1 | 5/2007 |
| WO | 2008048662 | A2 | 4/2008 |
| WO | 2008079341 | A2 | 7/2008 |
| WO | 2012019000 | A2 | 2/2012 |
| WO | 2012033771 | A2 | 3/2012 |
| WO | 2014028541 | A1 | 2/2014 |
| WO | 2015169810 | A1 | 11/2015 |

OTHER PUBLICATIONS

Awan, et al., "Machine Learning-Based Prediction of Heart Failure Readmission or Death: Implications of Choosing the Right Model and the Right Metrics", ESC Heart Failure, DOI: 10.1002/ehf2.12419, vol. 6,, Feb. 27, 2019, pp. 428-435.

Bertens, Loes C.M., et al., "A Nomogram was Developed to Enhance the use of Multinomial Logistic Regression Modeling in Diagnostic Research", Journal of Clinical Epidemiology, vol. 71, Mar. 2016, pp. 51-57.

Bodhe, et al., "A Proposed Mobile Based Health Care System for Patient Diagnosis using Android OS", International Journal of Computer Science and Mobile Computing, vol. 3 Issue.5,, May 5, 2014, pp. 422-427.

Cheng, et al., "Risk Prediction with Electronic Health Records: A Deep Learning Approach", Proceedings of the SIAM International Conference on Data Mining, Jun. 2016, pp. 432-440.

Clockbackward, "Ordinary Least Squares Linear Regression: Flaws, Problems and Pitfalls", Jun. 18, 2009, 16 Pages.

Dua, et al., "Machine learning in healthcare informatics", vol. 56. Berlin: Springer, 2014, 334 Pages.

Grossman, Daniel, et al., "Learning Bayesian Network Classifiers by Maximizing Conditional Likelihood", Proceedings of the 21st International Conference on Machine Learning, 2004, 8 Pages.

Hileman, "Accuracy of Claims-Based Risk Scoring Models", Society of Actuaries, Oct. 2016, pp. 1-90.

McCarthy, et al., "The Estimation of Sensitivity and Specificity of Clustered Binary Data", Statistics and Data Analysis, SUGI 31, Paper 206-31, 2006, 10 pages.

Mojsilovic, et al., "Semantic Based Categorization, Browsing and Retrieval in Medical Image Databases", Proceedings of the International Conference on Image Processing, IEEE, 2002, 2002, pp. 145-148.

Pearson, et al., "Disease Progression Modeling from Historical Clinical Databases", Proceedings of the Eleventh ACM SIGKDD International Conference on Knowledge Discovery in Data Mining, Aug. 21-24, 2005, pp. 788-793.

Ribeiro, "Why Should I Trust You?", Explaining the Predictions of Any Classifier, DOI: http://dx.doi.org/10.1145/2939672.2939778, Feb. 16, 2016, pp. 1135-1144.

Schneider, Beth, "Enabling Advanced Analytics to Improve Outcomes", Truven Health Analytics, Aug. 23, 2012, pp. 1-46.

Shen, Jess Jiangsheng, "Using Cluster Analysis, Cluster Validation, and Consensus Clustering to Identify Subtypes of Pervasive Developmental Disorders", Queen's University, Nov. 2007, 119 Pages.

Soni, et al., "Using Associative Classifiers for Predictive Analysis in Health Care Data Mining", International Journal of Computer Applications (0975-8887), vol. 4, No. 5, Jul. 2010, pp. 33-37.

Su, Chengwei, et al., "Using Bayesian Networks to Discover Relations Between Genes, Environment, and Disease", Bio Data Mining, http://www.biodatamining.org/content/6/1/6, 2013, 21 Pages.

Suo, et al., "Risk Factor Analysis Based on Deep Learning Models", Proceedings of the 7th ACM International Conference on Bioinformatics, Computational Biology, and Health Informatics, Oct. 2-5, 2016, 10 Pages.

Tan, et al., "Cluster Analysis: Basic Concepts and Algorithms,", Introduction to Data Mining (Second Edition), Chapter 8, Feb. 2018, pp. 487-568.

Truven Health Analytics, "Flexible Analytics for Provider Evaluation", Solution Spotlight, 2017, 4 Pages.

Truven Health Analytics, "Modeling Studies: Published Articles and Presentations", 2016, pp. 1-6.

Truven Health Groups, "Enterprise Decision Support", Product Spotlight, 2012, 2 Pages.

U.S. Patent and Trademark Office, "Final Office Action Received", U.S. Appl. No. 15/465,542, Dec. 30, 2019, 54 Pages.

U.S. Patent and Trademark Office, "Final Office Action Received", U.S. Appl. No. 15/465,542, Jan. 4, 2022, 51 pages.

U.S. Patent and Trademark Office, "Final Office Action Received", U.S. Appl. No. 18/414,296, Jul. 10, 2024, 11 Pages.

U.S. Patent and Trademark Office, "Final Office Action Received", U.S. Appl. No. 15/465,550, Mar. 21, 2022, 12 Pages.

U.S. Patent and Trademark Office, "Final Office Action Received", U.S. Appl. No. 16/386,123, Mar. 31, 2023, 59 Pages.

U.S. Patent and Trademark Office, "Final Office Action Received", U.S. Appl. No. 16/724,264, Nov. 30, 2022, 11 Pages.

U.S. Patent and Trademark Office, "Final Office Action Received", U.S. Appl. No. 15/927,766, Oct. 6, 2020, 22 Pages.

U.S. Patent and Trademark Office, "Final Office Action Received", U.S. Appl. No. 15/465,550, Oct. 14, 2020, 15 Pages.

U.S. Patent and Trademark Office, "Non Final Office Action Received", U.S. Appl. No. 15/927,766, Apr. 30, 2020, 19 Pages.

U.S. Patent and Trademark Office, "Non Final Office Action Received", U.S. Appl. No. 15/465,550, Jun. 26, 2019, 7 Pages.

U.S. Patent and Trademark Office, "Non Final Office Action Received", U.S. Appl. No. 16/386,123, Jun. 28, 2022, 55 Pages.

U.S. Patent and Trademark Office, "Non Final Office Action Received", U.S. Appl. No. 15/465,550, Mar. 13, 2020, 12 Pages.

U.S. Patent and Trademark Office, "Non Final Office Action Received", U.S. Appl. No. 15/465,542, Mar. 19, 2019, 29 Pages.

U.S. Patent and Trademark Office, "Non-Final Office Action Received", U.S. Appl. No. 15/465,542, Apr. 1, 2021, 37 Pages.

U.S. Patent and Trademark Office, "Non-Final Office Action Received", U.S. Appl. No. 15/465,550, Jul. 29, 2021, 10 Pages.

U.S. Patent and Trademark Office, "Non-Final Office Action Received", U.S. Appl. No. 18/169,363, Jul. 7, 2023, 48 Pages.

U.S. Patent and Trademark Office, "Non-Final Office Action Received", U.S. Appl. No. 16/724,264, Mar. 21, 2022, 20 Pages.

U.S. Patent and Trademark Office, "Non-Final Office Action Received", U.S. Appl. No. 18/414,296, Mar. 22, 2024, 13 Pages.

U.S. Patent and Trademark Office, "Non-Final Office Action Received", U.S. Appl. No. 18/169,372, May 8, 2024, 16 Pages.

U.S. Patent and Trademark Office, "Notice of Allowance Received", U.S. Appl. No. 15/465,550, Aug. 16, 2022, 8 Pages.

U.S. Patent and Trademark Office, "Notice of Allowance Received", U.S. Appl. No. 15/465,542, Aug. 24, 2022, 11 Pages.

U.S. Patent and Trademark Office, "Notice of Allowance Received", U.S. Appl. No. 16/386,123, Dec. 13, 2023, 12 Pages.

U.S. Patent and Trademark Office, "Notice of Allowance Received", U.S. Appl. No. 15/465,550, Jan. 26, 2023, 8 Pages.

U.S. Patent and Trademark Office, "Notice of Allowance Received", U.S. Appl. No. 18/169,363, Mar. 27, 2024, 10 Pages.

U.S. Patent and Trademark Office, "Notice of Allowance Received", U.S. Appl. No. 16/724,264, May 22, 2023, 8 Pages.

U.S. Patent and Trademark Office, "Notice of Allowance Received", U.S. Appl. No. 15/927,766, Oct. 14, 2021, 9 Pages.

U.S. Patent and Trademark Office, "Notice of Allowance Received", U.S. Appl. No. 15/465,542, Oct. 28, 2022, 12 Pages.

U.S. Patent and Trademark Office, "Notice of Allowance Received", U.S. Appl. No. 16/724,264, Sep. 6, 2023, 7 Pages.

U.S. Patent and Trademark Office, "Restriction Requirement Received", U.S. Appl. No. 16/724,264, Oct. 7, 2021, 6 Pages.

U.S. Patent and Trademark Office, "Non-Final Office Action Received", U.S. Appl. No. 17/573,725, Sep. 9, 2024, 27 Pages.

(56) References Cited

OTHER PUBLICATIONS

U.S. Patent and Trademark Office, "Notice of Allowability Received", U.S. Appl. No. 18/169,372, Oct. 16, 2024, 2 Pages.
U.S. Patent and Trademark Office, "Notice of Allowance Received", U.S. Appl. No. 18/169,372, Sep. 25, 2024, 9 Pages.
Zhong, Yizhen, et al., "Characterizing Design Patterns of EHR-Driven Phenotype Extraction Algorithms", In 2018 IEEE International Conference on Bioinformatics and Biomedicine (BIBM), Madrid, Spain, 2018; doi: 10.1109/BIBM.2018.8621240, pp. 1143-1146.

* cited by examiner

| Event code (e.g. diagnosis code, procedure code, medication code) | Relative time | Age | Smoker | Diabetes 2 patient | CHF patient | Event Weight |
|---|---|---|---|---|---|---|
| CPT: 8151 | 3 months | 40-50 | No | Yes | No | 100 |
| CPT: 3722 | 4 months | 40-50 | No | No | Yes | 200 |
| CPT: 8154 | 2 months | 60-70 | Yes | Yes | No | 130 |
| ICD10: K76.89 | 8 months | 20-30 | No | No | No | 10 |
| ICD10: K76.89 | 10 months | 60-70 | Yes | Yes | Yes | 550 |
| ... | ... | ... | ... | ... | ... | ... |

FIG. 2

| # | Patient ID | Date of Procedure | Date of Alert | Score | Risk Factors |
|---|---|---|---|---|---|
| 1 | 3456213 | 04/30/2019 | 05/02/2019 | 963 High Risk | HISTORY OF APE, HEART CONDITION, AGE + BMI |
| 2 | 4362465 | 05/01/2019 | 05/02/2019 | 902 High Risk | HEART CONDITION, AGE + BMI |
| 3 | 1653233 | 04/28/2019 | 05/05/2019 | 890 High Risk | HISTORY OF APE, HEART CONDITION |
| 4 | 4574577 | 04/02/2019 | 05/07/2019 | 850 High Risk | HISTORY OF APE, HEART CONDITION, AGE + BMI |

FIG. 6

APPLYING PREDICTIVE MODELS TO DATA REPRESENTING A HISTORY OF EVENTS

CROSS-REFERENCE TO RELATED APPLICATIONS

This application is a nonprovisional application of U.S. Provisional Patent Application Ser. No. 62/658,868, filed on Apr. 17, 2018, and entitled "APPLYING MACHINE LEARNING MODELS TO EVENT HISTORY DATA BY APPLYING EVENT WEIGHTS AS A FUNCTION OF RELATIVE TIME OF EVENTS", which is hereby incorporated by reference.

BACKGROUND

A challenge in the health care industry is providing meaningful data, on a regular basis, to health care providers, patients, insurers, care managers and other entities, regarding health care outcomes of patients, quality of care by health care providers, and a variety of other health-related metrics. Recently, computer systems have been able to provide measures of health care outcomes and other health-related metrics, such as various types of outcome measurements, scores, categorization and classification, risk identification, and risk factors, for patients, and quality of care and other metrics about health care providers. Such computer systems generally use models which perform analytical computations on patient data, which include, but are not limited to, mathematical operations applied to data, classifiers, clustering algorithms, predictive models, neural networks, deep learning algorithms and systems, artificial intelligence systems, machine learning algorithms, Bayesian systems, natural language processing, or other types of analytical models applied to small or large sets of data. Generally, such a model receives data values for an entity for a plurality of input features and provides an output for the entity based on the received data values. Some types of models are trained using a training data set in which the outputs corresponding to a set of inputs are known.

SUMMARY

This Summary introduces a selection of concepts, in simplified form, which are described further in the Detailed Description below. This Summary is intended neither to identify key or essential features, nor to limit the scope, of the claimed subject matter.

Health care data, and other types of data about entities, often include data representing a history of events. An event is an occurrence, or a thing that has happened. Event data is the data representing the event, which includes data representing a type of the event, and data representing when that event occurred, such as a date or time or both, which can be absolute or relative values. The type of the event can be any data that can characterize, label, or categorize the event. In health care, examples of events include, but are not limited to, a doctor's visit, an order of a laboratory test, a recording of a laboratory result, a recording of a diagnosis, copying of previous diagnoses or events, a prescription of a medication, a surgery or other medical procedure. Examples of types of events include, but are not limited to, standard codes for diagnoses, laboratory results, medications, treatments, and procedures. An example of event data to represent an event is a combination of such a standard code and a date.

An entity also may have an outcome. An outcome can be any value associated with an entity, and optionally a time. An outcome has a set or range of possible values, and an entity has a value indicative of the outcome for that entity which is from this set or range or possible values. Examples of outcomes in health care include, but are not limited to, a classification, a diagnosis, a result of treatment, a ranking among entities, a cost of treatment or care, or any other medical value. An outcome can be known or unknown. A "known" outcome is a value indicative of the outcome for the entity which is actually known or has been reasonably and reliably estimated from known data for the entity.

Predictive models can be used to estimate values indicative of outcomes for entities where those values are unknown, based on data about entities for which values indicative of their outcomes are known. A predictive model is built or trained using the data about entities for which values indicative of their outcomes are known, and then the predictive model can be applied to data about other entities to estimate values indicative of their outcomes. In some implementations, the predictive model also can output data indicating a probability or confidence in the value indicative of the outcome.

As further described herein, a predictive model can be applied to data representing a history of events for an entity to compute a value indicative of an outcome related to a reference time for that entity. The predictive model has inputs that receives data values for input features derived from the history of events. The predictive model has an output that provides the computed value indicative of the outcome. The model is "predictive" in that it generates data for which actual data is not currently available, i.e., the value indicative of the outcome for the entity, based on available data, i.e., the data representing the history of events for the entity and any other data for the entity, such as demographic or medical data. Examples of what a value indicative of an outcome may represent include, but are not limited to: an inference of a characteristic of an entity, such as a diagnosis; an estimate of likelihood or risk; an estimate of a value that may be realized in the future, such as a future cost or future risk or other future value; or an estimate of something that occurred in the past or present for which data is not currently available; or other value for which the data does not include a currently measured value; or any classification or ranking according to any of the above. Thus, the output of a predictive model also may be called a predicted outcome, an estimated outcome, an inferred outcome or similar term.

The relative time of an event with respect to a reference time, such as the current time, is the difference in time between when the event occurred and the reference time. The effect of an event from an entity's history of events on an outcome for the entity at a reference time can vary based on the type of the event and the relative time of that event with respect to the reference time. Thus, when building a predictive model which computes a value indicative of an outcome at a reference time for an entity based on a history of events for that entity, it would be desirable for the output of the predictive model to reflect the impact relative times of events with respect to the reference time can have on the outcome.

The effect of an event from an entity's history of events on an outcome for the entity also can vary due to other characteristics of the entity in combination with the event. For example, with health care data, the effect of an event on an outcome can vary across different patient cohorts defined by various characteristics. Different patient cohorts can be defined, for example, by different demographic profiles, such as age, gender, and family history of disease. Different patient cohorts can be defined, for example, by different medical conditions, such as comorbidities, such as diabetes, obesity, congestive heart failure, or genetic profile, such as the presence of certain sequence in the patient's DNA. Thus, when building a predictive model which computes a value indicative of an outcome for an entity based on a history of events for that entity, it would be desirable for the output of the predictive model to reflect the impact such characteristics can have on the outcome.

The characteristics which are selected to be included among those characteristics of an entity which are used to modify the effect of an event on a predicted outcome for the entity are called herein "entity profile characteristics". These entity profile characteristics can be any data about an entity that is selected to be used. With health care data, examples of entity profile characteristics include, but are not limited to, demographic data and medical conditions. In some cases, a medical condition (such as diabetes) can be treated both as an entity profile characteristic (data may indicate a patient has this condition) and as an event (diagnosis codes may occur in the history of event data for the patient). In some cases, other patient data, such as age, can be treated both as an entity profile characteristic and as an input feature to the predictive model.

Building a predictive model using, and applying a predictive model to, data representing a history of events, using combinations of event data with relative time of events and/or entity profile characteristics introduces several complexities. For example, using every single type of event as input (predictive feature) to the model results in very large number of inputs to the predictive model. The number of inputs increases manifold when we include multiple relative times for each event.

A predictive modeling algorithm would have to simultaneously learn the effects of every type of event and for multiple relative times. The presence of large numbers of inputs (predictive features) causes a strain on these algorithms and often leads to suboptimal predictive models. Also, the importance of a relative time of an event generally is specific to that event, e.g., the importance of a relative time is different for a cardiac event, for a surgery, or for a genetic test. Thus, different kinds of events have different relative times that are relevant. Furthermore, if entity profile characteristics are used as stand-alone predictive features that are direct inputs to the predictive model, then the model has increased difficulty learning the different effect of each entity profile characteristic in combination with each type of event and relative time; if the entity profile characteristics enter the model in the form of interactions with type of events or relative times or both, then there would be a significant increase in the number of inputs to the predictive model and there would be further strain on the capability of the predictive model to optimize the predictive performance of the resulting model. These complexities could make it difficult to train a predictive model.

Given an adequate volume of data for cohorts defined by different combinations of types of events, relative times of events with respect to a reference time, and entity profile characteristics, dependencies of outcomes on these combinations can be represented in data that are computed directly from the history of event data and then input to the predictive model. Thus, instead of using various data as direct inputs to a predictive model, a computer system computes, for an entity, one or more functions of one or more set of events from the history of events for the entity and a set of weights for these events. The computed results are the inputs to the predictive model. Effectively, instead of predicting a patient's outcome as a function of the combination of events and conditions in the patient's history, the system learns effects of events and conditions (in the weight tables) and in turn predicts a patient's outcome as a function of the combination of the effects of these events and conditions. The number of inputs to the predictive model depends on the number of functions and the number of sets of events used, and not on the number of relative times computed, the number of types of events in the data, or the number of entity profile characteristics used.

In some implementations, the set of weights includes weights corresponding to tuples that represent different combinations of types of events, relative times of events, and entity profile characteristics. A weight is specified in the set of weights for each tuple. A tuple can have more than one corresponding weight. In some implementations, a weight is specified for a combination of a type of event with a relative time and/or an entity profile characteristic. A weight may be associated with a type of event, a type of event with a relative time, a type of event with an entity profile characteristic, or a type of event with both a relative time and an entity profile characteristic. The set of weights can be stored in a weight table in which a tuple has a corresponding row including data representing the tuple and data representing the weight or weights for the tuple, in one or more other columns.

In the set of weights, different weights may be specified for a type of event when an event of that type occurs with different relative times with respect to the same reference time. For example, an event such as a surgery may have one weight if the event occurred one month from the current time compared to if the event occurred two years from the current time. Different weights may be specified for a type of event when an event of that type occurs with different reference times, such as one year from the current time versus one year from a surgery. Different weights also may be specified for a type of event when an event of that type occurs in different combinations with entity profile characteristics of the entity. For example, an event such as a surgery may have one weight if a patient also has a diagnosis of diabetes, and a different weight if a patient does not have diabetes, provided that diabetic status is used as an entity profile characteristic.

For example, given a set of medical events that may occur in a patient history, such as the combined sets of ICD10 diagnosis codes and CPT procedure codes, a set of entity profile characteristics, and a set of relative times, such as {0 months, 1 month, . . . , 20 months}, the system provides weights for unique combinations of values from the three sets. A weight is intended to capture an effect of a specific medical event in a patient history, for a patient with given entity profile characteristics or when the medical event occurs at a specified time with respect to a reference time, on a medical outcome related to the reference time or on a medical value that is associated with the patient and related to the reference time, e.g., a total expenditure for a patient over a year starting from the reference time.

In some implementations, weights for relative times may be at a temporal resolution and/or temporal range which is different from relative times desired to be used when applying the predictive model. For example, weights may have been computed for relative times occurring at one-month intervals for a period of two years from a reference time. When using the weights, it may be desirable to have relative time data that is, for example, for a period of three years, or, for example, occurring at one-week intervals. A form of interpolation and/or extrapolation applied to the set of weights can be used to obtain other weights corresponding to relative times not represented in the set of weights.

In both training a model and applying a model, one or more sets of events are extracted from data representing a history of events for an entity. Relative times for events in those sets of events can be calculated with respect to a reference time. Weights for the events in the sets are retrieved from the set of weights based on combinations of the events with any relative times and/or any entity profile characteristics. Given a set of events, the computer system computes one or more quantities using one or more functions of the weights for the events included in the set. Such a function can be, for example, a linear function, such as a weighted sum, or a nonlinear function, such as a maximum. The quantities computed for the set of events for the given entity are part of the input to the model for the model to compute a value for the outcome for that entity.

Using functions to compute quantities based on set of weights and a history of events, and providing the computed quantities as inputs to a predictive model, the computer system can efficiently build predictive models using, and can apply those predictive models to, data representing a history of events for entities, such as patient medical data, while incorporating relative time of events and entity profile characteristics.

The set of weights and the predictive model for predicting an outcome are trained using data sets for entities for which values indicative of the outcome is known. Preferably, separate data sets are used for training the set of weights and for training the predictive model. The weights are trained first, and then used in the training of the predictive model.

To train a set of weights, a weight table training module selects events from the training set. For a selected event for an entity, a relative time for the event with respect to a reference time is computed, and an outcome for the entity related to the reference time is computed based on the known outcome for the entity. For a tuple representing a combination of a type of event, a relative time, or an entity profile characteristic, a weight for the tuple is computed based on the computed outcomes related to the selected events corresponding to the tuple. The weight also can be based on data indicative of a number of entities having the selected events corresponding to the tuple and/or a number of times the selected events appear in the histories for these entities.

Such a predictive model also can be subjected to further analysis, for a selected entity or set of entities, to explain which features (including events) in each entity's data most affect the outcome of the predictive model. In some implementations, the computer system can personalize the predictive model with respect to the selected entity using data values for the selected entity. The computer system inputs one or more different data values for selected input features of the personalized model, while data values for the remaining input features of the personalized model are fixed to data values for the selected entity. The effect of the different data values for the selected input features on the outcome predicted by the model can be determined and information related to this effect can be communicated to a user.

In the following Detailed Description, reference is made to the accompanying drawings which form a part of this disclosure. These drawings show, by way of illustration, example implementations. Other implementations can be made without departing from the scope of this disclosure.

BRIEF DESCRIPTION OF THE DRAWINGS

FIG. 2 is an example implementation of a data structure representing a weight table.

FIG. 6 is an example graphical user interface for a computer that accesses the computer system.

DETAILED DESCRIPTION

Referring to FIGS. 1A-D, a data flow diagram of an example implementation of a computer system, which applies predictive models to data representing a history of events, will now be described. The predictive model outputs a value indicative of an outcome. An outcome may represent an inference of a characteristic of an entity, such as a classification or diagnosis, an estimate of likelihood or risk, an estimate of a value that may be realized in the future, such as a future cost or future risk or other future value, or an estimate of something that occurred in the past for which data is not currently available, or other value for which the data does not include a currently measured value.

Figure 1A:
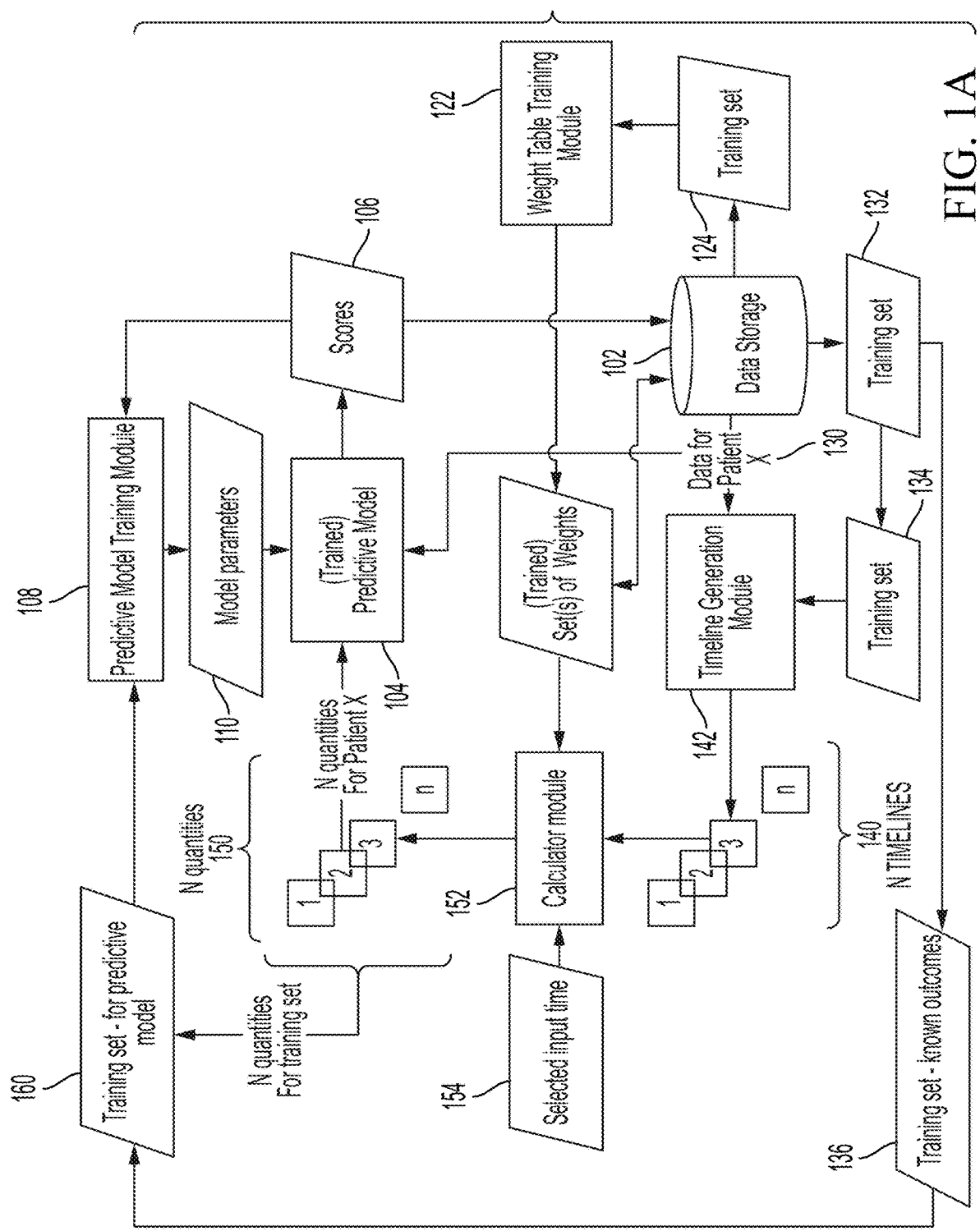
FIG. 1A is a data flow diagram of an example computer system supporting applying predictive models to data representing a history of events.
Figure 1B:
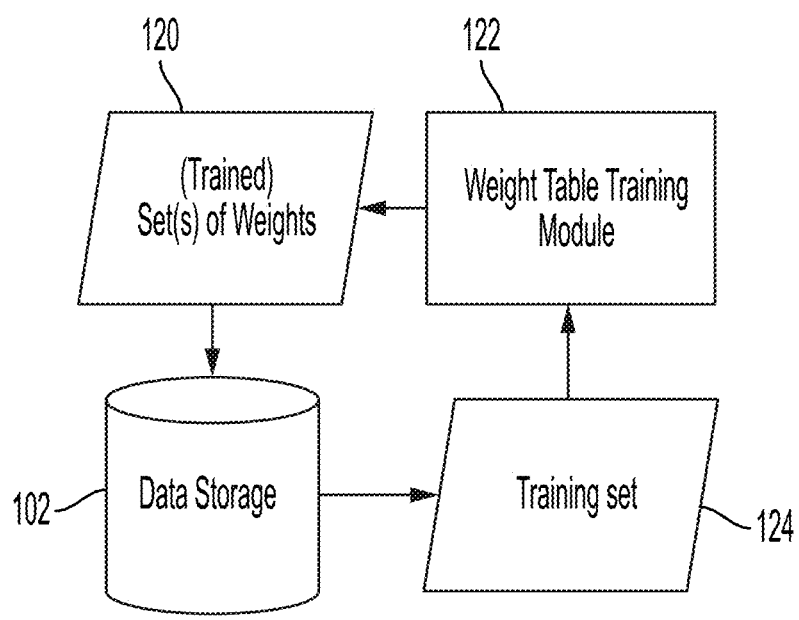
FIG. 1B is a data flow diagram illustrating components of FIG. 1A used for training a set of weights.
Figure 1C:
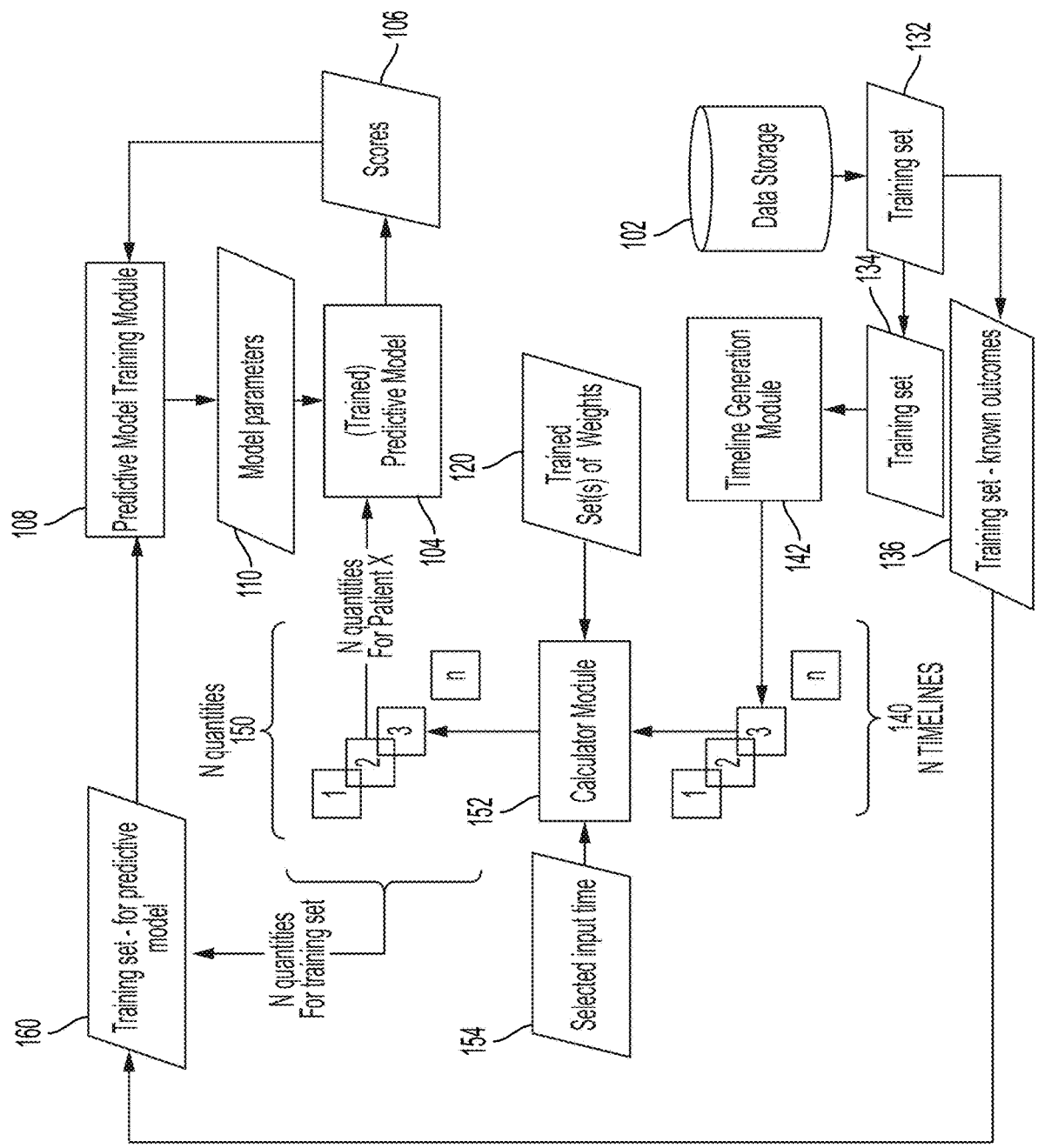
FIG. 1C is a data flow diagram illustrating components of FIG. 1A used for training a predictive model given a trained set of weights.
Figure 1D:
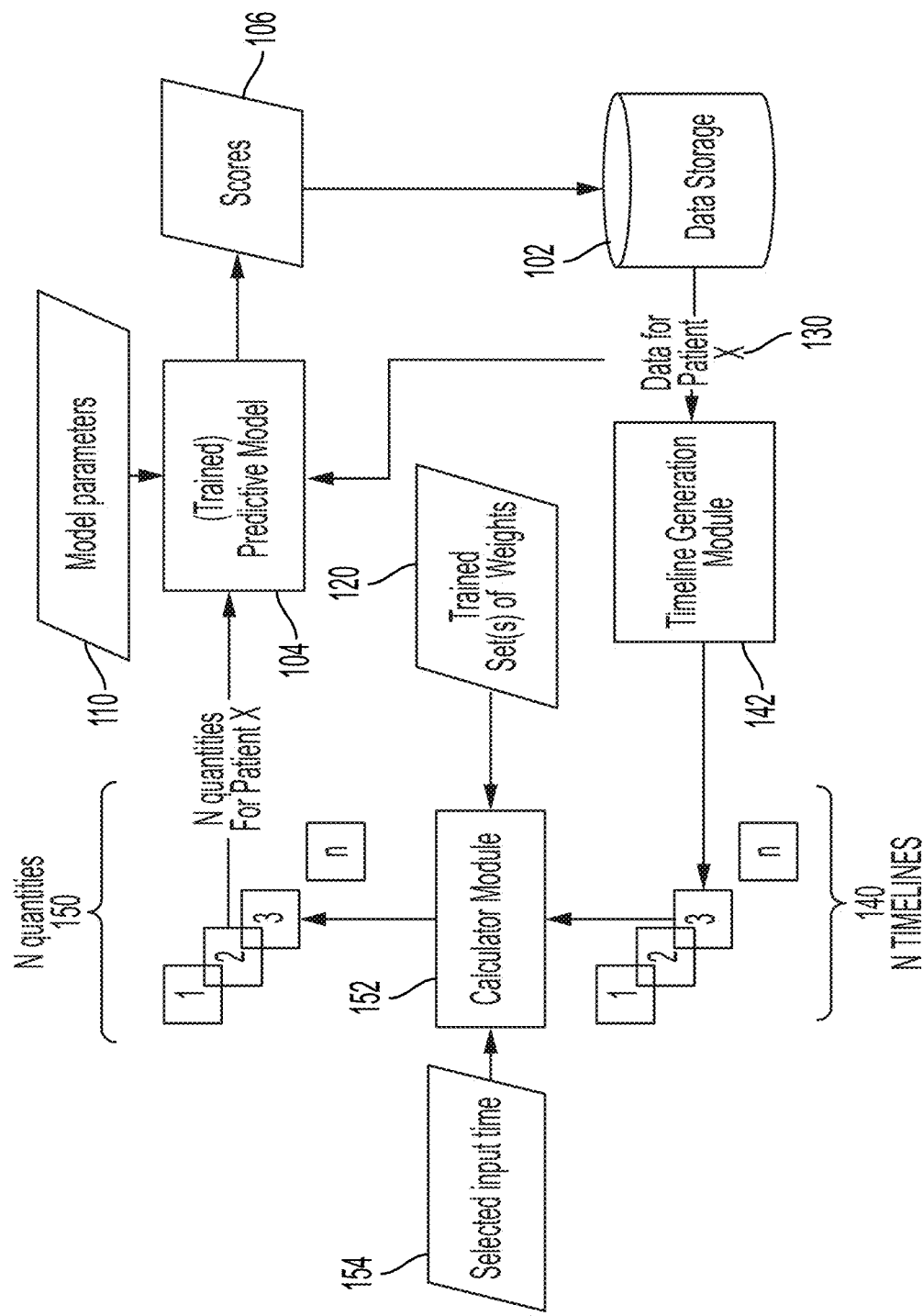
FIG. 1D is a data flow diagram illustrating components of FIG. 1A used for applying a trained predictive model using a trained set of weights to entity data.

This computer system as illustrated in FIG. 1A incorporates components for training a set of weights, for training a predictive model, and for applying a trained predictive model to entity data. It should be understood that separate computer systems can be deployed which separate the operations of training a predictive model, the operations of training a set of weights, and the operations of applying a trained predictive model. FIG. 1B is a data flow diagram illustrating components of FIG. 1A used for training a set of weights using a weight table. FIG. 1C is a data flow diagram illustrating components of FIG. 1A used for training a predictive model given a trained set of weights. FIG. 1D is a data flow diagram illustrating components of FIG. 1A used for applying a trained predictive model using a trained set of weights to entity data.

A computer system 100 as shown in FIG. 1A includes data storage 102 which can store data sets for entities. The computer system uses such data sets to compute outcomes using a trained predictive model, and/or as training sets to train one or more predictive models or to train a set of weights.

Such data can include, for example, health care information for a plurality of patients. The health care information for a patient can be obtained from a number of different sources of health care information for the patient including electronic medical records from the patient's health care providers, insurance providers and other sources. More particularly, health care information can include, but is not limited to, information recorded for patients by a health care provider. Examples of health care providers include, but are not limited to, individuals, such as a physician, a therapist, a nurse, or support staff, and organizations, such as a hospital or other facility employing health care providers. Health care information can include information from entities other than health care providers but who are otherwise involved in health care, such as insurers, laboratories, supply providers and the like, which may store information about claims, diagnostic tests, laboratory work, suppliers and vendors. Health care information can include information reported by patients and/or their caregivers. Such health care information generally includes demographic information and medical information.

The demographic information can include, for example, age, gender, race, family history including medical history, social history, and other information for the patient. If personally identified information authorized and stored, such information can include a name, an address and various contact information.

The medical information can include, for example, information about reported or observed symptoms of the patient, diagnoses made and/or recorded by health care providers, any medications, treatments and other interventions prescribed or recommended by a health care provider, and/or any requests for laboratory work or diagnostic tests, related reports or results, and family medical history. Such data can be stored as a history of interactions with the health care provider and may have multiple instances of a type of data over time, such as vital signs and lab results. Such data typically includes information, typically representing symptoms, diagnoses, procedures and medications, which is typically coded according to a standard, such as ICD-9, ICD-10, CPT, SNOMED, LOINC, COSTAR, and RxNorm coding systems. Family medical history also may be included, as well as provider data, including statistics of outcomes per provider.

Such health care information can be de-identified data such that any personally identifying information is removed, in which case the health care information for a patient is associated with a unique code representing that patient, which code distinguishes the patient from other patients.

Such health care information generally includes both structured and unstructured data. Structured data generally is data that has a specified data model or other organization, whereas unstructured data generally does not. By way of example, structured data can include database records, attribute-value pairs, and the like, whereas unstructured data can be either textual data, such as free text, documents, reports of results, published and unpublished literature, and the like, or non-textual data, such as image data of which DICOM data is an example.

Health care information also can include cost information related to resources for various activities related to providing health care for a patient. Thus, for each activity performed with respect to a patient, resource utilization information also can be made available. Resources can include personnel, equipment, supplies, space, and the like. Resources generally have an associated cost, typically represented by a cost per unit, cost per unit of time, cost per unit of space, and the like.

The data storage 102 can include a database that stores data about entities. The database generally stores the data as collections of data fields which store values, in a structured or semi-structured manner, within sources, such as in tables within a relational database, in objects within an object-oriented database, in key-value pairs or columns in structured data files within a NoSQL or similar database, or in streams or similar file system objects within a streaming storage system or distributed file system, or in binary large objects. An example distributed file system can be a distributed file system in the HADOOP framework, with large file system objects and an implementation of a computational paradigm called Map/Reduce to perform operations on such file system objects. The database typically also has a technology to query the stored data, such as the Structured Query Language (SQL).

In some implementations, the data storage 102 can be implemented using the a secure, cloud-based data warehousing system which provides relational database support for structured and semi-structured data. Such a system can provide scalable data storage with support for SQL based queries.

The database generally is stored on a computer, such as described below in FIG. 4, that is configured to allow access to the data storage by other computers through defined transactions, typically over a computer network. The computer also can be programmed to perform database operations on the database as part of such transactions. Such a computer supporting the database is configured with sufficient processors, memory and storage to support storage of data in, and access to that data from, data storage 102.

The data storage 102 can include data from multiple storage systems (not shown) for each of multiple entities. While data from multiple entities can remain stored in their respective storage systems, such data can be consolidated in data storage 102. In some implementations, the data is not consolidated, but remains in distributed entities that can be logically combined for processing, but without consolidating the data into a single database system. Multiple storage systems of multiple entities typically are distributed geographically, so such consolidation can occur by requests for transmission of data over one or more computer networks (not shown) to the data storage 102. Such requests can be periodic, or irregular, or can be made when the data is to be used by the computer system 100. Thus, data storage 102 can include any computer storage that can temporarily store data for entities received from remote computers.

The computer system includes a predictive model 104, which is generally implemented on one or more general-purpose computers, such as described below in connection with FIG. 4, using computer program code processed by a processing system of the computer. When processing the computer program code, the processing system implements a predictive model that computes values indicative of an outcome for entities based on data values for input features derived from data for the entities. In health care, such outcomes can include future resource utilization, risks of future conditions occurring, risks of future events, classifications, diagnoses, imputed data, and the like. The predictive model 104 processes data derived from entity data from the data storage 102 to compute scores 106, which are values indicative of an outcome. The computer system can be programmed to train a predictive model 104 and/or apply a trained predicted model 104 to entity data.

The computer system shown in FIG. 1 can be incorporated into a larger computer system, such as one described in U.S. patent application Ser. No. 15/927,766, entitled "Information System Providing Explanation of Models", filed Mar. 21, 2018, which is hereby incorporated by reference.

The predictive model 104 can be built using any of family of algorithms described as supervised classification or machine learning or econometrics algorithms or deep learning, which perform functions such as classification, prediction, regression or clustering. With such algorithms, a computer generates a model based on examples with known (whether actually known or reliably estimated) outcomes provided in a training set. Any supervised classification or machine learning or deep learning model can be used as a classifier, such as support vector machines, conditional random fields, random forest, logistic regression, decision tree, maximum entropy, artificial neural networks, genetic algorithms, or other classifier or predictive model, or combination of such models, for which parameters of a function can be trained by minimizing errors between values output by the model for entities and known outcomes for those entities, using a set of training examples. Such models generally produce a score, which is a value indicative of an outcome, and may also provide a probability or confidence value. In some implementations, the score and probability or confidence value are one and the same value.

The data storage 102 can include a server computer (not shown) implemented using a general-purpose computer such as described below in connection with FIG. 4 to control access to data by other components of the computer system. The data storage 102 also can be accessed through one or more server computers over a computer network through an application programming interface. A server computer can be implemented using a general-purpose computer such as described below in connection with FIG. 4. The general-purpose computer is configured as a server computer, with sufficient processors, memory, storage and communication connections. In one example implementation, the server computer can be configured to operate as a "Web" server, or a server computer that implements a hypertext transfer protocol (HTTP) or secure hypertext transfer protocol (HTTPS), using a computer program such as the Apache web server computer program or other similar web server computer programs.

The computer system trains the predictive model 104 using a training process implemented within a predictive model training module 108. This module generally is implemented as computer program code processed by a processing system of a computer system, such as shown in FIG. 4. The computer program code implements the training process through which model parameters 110 of the predictive model 104 are repeatedly adjusted so that, given a set of input data for entities with known outcomes, called a training set, the output scores 106 from the predictive model 104 substantially match the known outputs for that training set of input data, within some range of acceptable error.

In this computer system, the predictive model 104 is applied to data derived from a history of event data for an entity, which can include types of events in combination with relative times of events and/or entity profile characteristics. The output of the predictive model 104 is a score 106, which is designed to optimize prediction, estimation or inference of an outcome. The score can be computed using the history of event data for the entity. In turn, the score is a value that is indicative of an outcome, and thus may be understood as a prediction, estimate, or inference of the outcome. This prediction, estimation, or inference of an outcome typically is used in cases where the outcome for a given entity is not directly computable based on the history of events for the patient. For example, the outcome to be inferred can be future resource utilization, based on currently available patient profile characteristics.

As noted above, the data storage 102 includes data for a plurality of entities. The data can be comprised of data records, where a data record includes data values for a plurality of data fields in a database. Some data records represent event data which are used to compute inputs to the predictive model. A data record representing an event for an entity includes data representing an occurrence of a type of event at a point in time in a history of events for the entity. Some data records may include other data for the patient, such as demographic information and/or medical information. Some data in the data records may be used as entity profile characteristics for specifying weights in a set of weights. For some types of events, a relative time can be computed with respect to a reference time. For example, in patient data, an event may specify a type of event, such as an admission to a hospital, a lab result, a surgery, etc., which is associated with a date, or time, or both. Given a set of types of events, the computer system can compute relative times for events in an entity's history of events. Computed relative times can be stored in the data storage 102.

The relative times computed with respect to a reference time generally are not constant and therefore may be updated frequently. For example, the relative times can be computed daily as a batch process applied to all entity data. The frequency of update to the relative times can be selected based on the precision of calculation of the relative times and can be different for different types of events or different outcomes to be predicted. Such relative times also can be computed "on demand" at the time the information is needed when analyzing the data for a selected entity. For example, a health care provider may use the computer system to access predictive data generated by the predictive model for a selected patient at the time of the visit from the patient. As another example, the reference time can be a point in the past, and can vary from patient to patient, such as the time of a surgery for a set of patients who have undergone this surgery.

The tuple of a type of an event in combination with a relative time of the event and/or an entity profile characteristic, is assigned a weight. A weight may be associated with a type of event, a type of event with a relative time, a type of event with an entity profile characteristic, or a type of event with both a relative time and an entity profile characteristic. The weight is a measure of impact of the presence of such an event in the patient profile or history on the outcome for the entity. There can be multiple different weights for a specific type of event based on different relative times and/or different entity profile characteristics considered. In other words, the weight for an event for a given entity can be dependent on, or be a function of, one or more relative times and/or entity profile characteristics in the data record for that entity. For example, in health care data, a weight can be assigned to a type of an event in combination with other data such as: a relative time of the event with respect to a reference time, age, gender, and/or location of the patient, comorbidities and/or behavioral data. For example, the weight assigned to an event that is a surgery can be a function of that type of event, its relative time with respect to a reference time, and presence of other features in the patient medical data, such as patient demographic information, such as age or gender, or other patient conditions, such as diabetes, smoking, heart disease and obesity. Note that this explanation of combinations of types of events and additional entity profile characteristics is based on an example of a patient. Such combinations can be created for other entities, such as health care providers or other entities.

It should be noted that the relative time of an event with respect to another point in time can impact the weight for a particular outcome differently depending on the event. A patient experiencing a myocardial infarction will be more at risk if they were to undergo a surgery two weeks after such an event than if they were to undergo that surgery two years after the event. In contrast, certain events, such as the onset of type II diabetes may increase risk the longer the time period is from onset to the reference time used in the predictive model.

For example, if the computer system is set up to infer the future resource utilization in a period from May 1, 2018 to Apr. 30, 2019, the time of a certain procedure in relation to the starting date May 1, 2018 makes a difference. For example, if a total knee replacement occurs on Apr. 15, 2018 the expected correlation of that procedure on the future resource utilization is different from the expected correlation of a total knee replacement that may have occurred on, e.g., Sep. 15, 2017.

As another example, the effect of an event on an outcome usually varies by age of the patient. The effect of an event on an outcome also can vary by comorbidities. For example, the expected effect on an outcome of a heart surgery for a type 2 diabetic may be different from the expected effect for a patient without the type 2 diabetic condition.

As another example, the effect of an event on an outcome also can vary by behavioral attributes such as smoking. For example, the expected effect of a heart surgery for a smoker may be different from the expected effect for a patient who is not a smoker. The additional factors that may affect the weight assigned to an event in an entity's history can be identified in several ways, such as expert opinion, data analysis, medical literature and the like.

In some implementations, to provide such a capability the computer system includes one or more sets of weights 120. The set of weights can be implemented using any data structure that can store in memory, for a plurality of types of events, weights for tuples representing different combinations of a type of event with at least one of a relative time with respect to a reference time or an entity profile characteristic. Thus, a weight may be associated with a type of event, a type of event with a relative time, a type of event with an entity profile characteristic, or a type of event with both a relative time and an entity profile characteristic. A suitable data structure allows the weight for a tuple to be accessed readily using the data defining the tuple.

An example implementation of a set of weights is a weight table. FIG. 2 shows an illustrative example of a weight table 200 for illustration purposes. Each row, e.g., 202, of the table provides a weight 250 for a tuple of a type of event 210 in combination with at least one of a relative time 212 for that event and/or other entity profile characteristic. A plurality of weights 250 can be associated with and stored for each tuple. In this illustrative example, the other entity profile characteristics include age 214, smoking status 216, and comorbidities of diabetes 218 and congestive heart failure (CHF) 220. Thus, as shown in this illustrative example, if a patient has the combination of an event code of "CPT:8151" at a relative time of 3 months, and age between 40 and 50, as a non-smoker, with diabetes and no congestive heart failure condition, the weight of "100" as assigned to the event "CPT:8151" for that patient.

The example weight table in FIG. 2 includes only a few examples out of potentially millions of rows which cover all combinations of types of events (e.g., diagnosis codes procedure codes, medication codes, lab diagnosis within a certain range of interest, genetic information etc.) which can be included in such a table. To manage combinatorial expansion of this table, from the perspectives of both storage and computation of relative time data and weights, for all combinations of types of events, relative time data and any entity profile characteristics, the computer system is limited in the number of columns allowed in the table, and in the number of rows added by the number of relative time values that are used for a type of event. Another way to limit the columns is by defining medical instances (described below) as combinations of events and/or entity profile characteristics and providing a single row for data representing a medical instance in lieu of multiple rows in the table. By limiting the number of columns, the number of possible combinations is limited, which in turn limits the number of rows in the weight table. Similar restrictions can be applied to other data structures implementing a set of weights. Further, the computation can be performed using a "big data" system as described in more detail below.

In some implementations, a method for representing the events in a patient history is by aggregating event codes into categories of event codes, herein called "medical instances". A "medical instance" (MI) is a collection of event codes that enables weights to be assigned to the collection instead of each individual event code. In some implementations, a medical instance can be a single event code. In some implementations, a medical instance can be a group of event codes, which can be a combination of standardized codes from different sets of standardized codes. An entire set of individual event codes can be transformed into a smaller set of groups of these event codes. Example approaches to deriving medical instances are described below. In this example implementation, medical instances are defined as groups of event codes.

In this implementation, a medical instance comprises a set of event codes which are related to each other in some way. This results in few medical instances where each event code within the medical is related to the other event codes within the medical instance using the type of the event code.

Another kind of medical instance represents a relation of co-occurrence. A medical instance can be a collection of event codes which are present in patient medical histories more frequently with each other than they are present with other event codes which are used to define other medical instances. There are various algorithms that can be used to generate a set of medical instances by optimizing grouping of codes with regards to co-occurrence.

In some implementations, a patient medical history can be organized and represented as an ordered sequence of events, in which events are ordered with respect to time at which they occurred in the patient medical history. Such ordering sometimes cannot be strict due to multiple codes having identical timestamps. In that case, there can be secondary ordering based on some other criteria (e.g., by type of code) or simply random secondary ordering. Given a set of ordered patient medical histories, the codes in the list of codes can be mapped onto a Euclidean embedding space for which the dimensions have been predetermined by the user. This mapping can be optimized such that the more frequently two codes are found in high proximity to each other in patient histories, the closer their mapped embeddings reside in the embeddings space. Such algorithms may come in various forms.

After such embeddings have been produced, medical instances can be produced by splitting the embeddings space into sub-spaces each of which holds a cluster of embeddings. Such splitting can be produced by using unsupervised learning methods from the fields of machine learning, statistical learning, artificial intelligence, deep learning or combinations thereof. Unsupervised learning is a collection of clustering algorithms which optimally split up a Euclidean embeddings space in subspaces by drawing a number of hypersurfaces which serve as the boundaries of the various subspaces. The number of resulting subspaces is either pre-specified by the user or optimally selected by the clustering algorithm, depending on the use case and/or the algorithm. There is a large variety of clustering algorithms, as discussed above. Examples include k-means, k-medians, expectation maximization clustering using Gaussian mixture models, agglomerative hierarchical clustering, density-based spatial clustering of applications with noise (DB-SCAN), deep embedded clustering and many others. Each one of these algorithms can be used to derive medical instances as described above. In some implementations, k-means clustering and vector-based word embeddings can be used to generate medical instances.

Implementations which generate medical instances on the basis of co-occurrence relations include algorithms derived from approaches such as count-based methods (e.g., latent semantic analysis), and predictive methods (e.g., neural probabilistic language models). The methods of representation that use co-occurrence relations have the underlying hypothesis that medical codes which appear in the same patient medical histories relate to similar medical context or, in other words, similar conditions.

Relations other than co-occurrence of medical events in patient medical histories can be used to guide the automated generation of medical instances that are groups of medical codes or events. Different algorithms from artificial intelligence, machine learning, deep learning and others may be used to generate medical instances based on such relations.

Medical instances also can be generated by human experts fully or partly. In that case, the medical experts use criteria that guide them to group event codes into medical instances. For example, the criterion may be to ensure that event codes which relate to the same condition are in the same group. A variety of criteria may guide human experts in their generation of medical instances. In some cases, a hierarchy of code definitions may serve this purpose.

There are cases where medical instances are generated using a combination of algorithms and human expertise. Human experts can adjust or alter medical instances generated by the computer or can pre-process the data that is used by automated algorithms to generate the medical instances.

In some implementations, the set of generated medical instances may be algorithmically altered and fine-tuned, for example by using algorithms that judiciously rearrange the event codes of specific medical instances, or by merging some medical instances into larger medical instances, or by dividing some medical instances to smaller medical instances in order to satisfy size or coherence criteria.

Multiple different sets of weights can be constructed for different types of outcomes to be predicted. For analyzing health care data and predicting health care outcomes, separate sets of weights can be created, for example, for: future resource utilization (e.g., total medical costs) of a patient over one year starting at a certain day in the present or future; future mortality within a period over one year starting at a certain day in the present or future; future cost (e.g., within a period over two years starting at a certain day in the present or future) of inpatient hospitalizations; future probability of emergency room visits; concurrent estimation (e.g., within a period over two years starting at a certain day in the past) of total medical cost of a patient given their medical history over a concurrent period of time. In some instances, the predicted outcomes are not in the future but may be predicted current outcomes or other information for the patient, which are imputed to the entity.

A set of weights can be computed in several ways. In the example implementation shown in FIGS. 1A and 1B, a weight table training module 122 is provided to generate one or more sets of weights 120. The weight training module 122 receives a training set 124 of data from the data storage 102. The training set includes data records for entities for which their data records include events and known outcomes.

Figure 4:
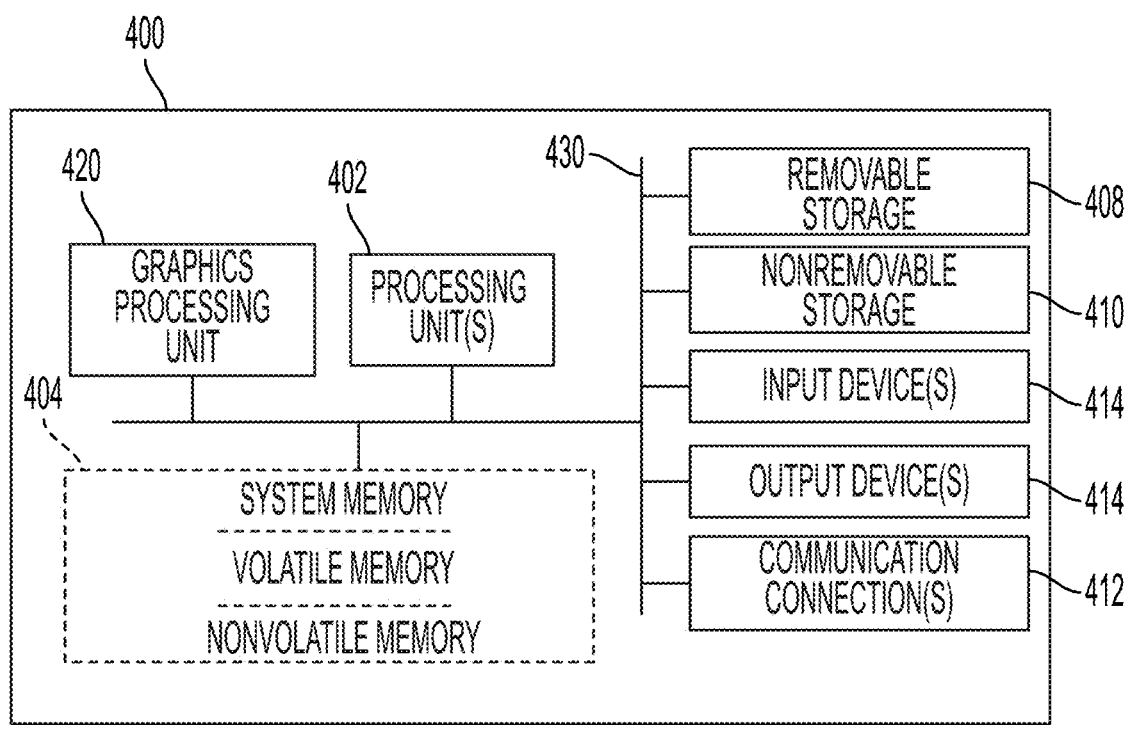
FIG. 4 is a block diagram of an example computer.

The weight table training module is implemented as computer program code processed by a processing system of a computer system, such as a general-purpose computer such as in FIG. 4. The computer program code, when processed by the processing system, configures the computer system to implement the process described below, and to allocate memory and storage for data structures that store data used and generated by the process. Generally, a weight table training module selects events from the training set used for weight training. For a selected event for an entity, a relative time for the event with respect to a reference time is computed, and an outcome for the entity related to the reference time is computed based on the known outcome for the entity. For a tuple representing a combination of a type of event, a relative time, or an entity profile characteristic, a weight for the tuple is computed based on the computed outcomes related to the selected events corresponding to the tuple. The weight also can be based on data indicative of a number of entities having the selected events corresponding to the tuple and/or a number of times the selected events appear in the histories for these entities.

An example implementation of the weight table training module will now be described, where the set of weights is implemented as a weight table. A weight calculation table, similar to the weight table to be created, is initialized with columns for each of the type of event, a relative time for the event and each entity profile characteristic. The weight calculation table, instead of including a column for a weight, includes two columns: an outcome column in which known outcomes from entities in the training set are aggregated, and a number of occurrences column, each of which are initialized to zero (0) for all rows.

For each entity (in this example, each patient) in the data set, the computer system extracts a set of events for the patients. This set of events can have appropriately specified date bounds (e.g., Jan. 1, 2013-Dec. 31, 2015). The specification of types of events, comorbidities and other entity profile characteristics, and date bounds can be established in many ways, such as a configuration file or as user input received interactively through a user interface. In this example, for events in the extracted set of events for a patient, the following are computed: the age of the patient at the time of that event, whether the patient has any of the specified entity profile characteristics, such as comorbidities established at the time of the event or behavioral (such as smoking) statuses at the time of the event. This step allows a determination of which row of the weight table will be affected by the training data from this patient.

Next, given an event for a patient, for different relative times, e.g., 1 month, 2 months, 12 days, 41 days, etc., for the event, the training module computes a value indicative of the outcome of that patient corresponding to a time which is equal to the sum of the time of the event and the relative time. As an illustrative example, given a patient with an event of a myocardial infarction (MI) on in January 2017, and a relative time of one month (thus, February 2017), and an outcome representing costs of care for the coming year, the training module computes, from the known outcome data for the patient, the cost of care for that patient for the period of February 2017 through February 2018. Then, the training module also updates the value of the outcome column of the corresponding row of the weight calculation table based on the computed value for the outcome for that entity for that relative time. The computer also increments the number of occurrences column for that row by 1. This step introduces a way to address the dependence of the weights on relative time.

In some implementations, the training set can be processed to create the weight calculation table by adding rows to the weight calculation table as unique combinations of events, relative times, and entity profile characteristics are encountered in the training set.

After processing the events for the patients in the training set 124, for each row in the weight calculation table, a weight is derived. The weight may be derived using any of a variety of functions, but generally as a function of the aggregated outcomes in the outcome column. The function can include data indicative on a number of entities and/or a number of events corresponding to the row of the weight calculation table. In some implementations, the function can be linear. In some implementations, the function can include an average, such as computing the weight by dividing the aggregated outcomes from the outcome column by the number of occurrences. As an example, the number of occurrences can represent a number of entities or a number of events. In some implementations, the function can be non-linear, such as a limiting function, such as a maximum or a minimum. The training module 122 stores the computed weight as the weight 250 in the weight table 200 in a corresponding row.

Turning back to FIG. 1A, the score 106 output by the predictive model 104 is designed to combine the estimated effect of each event in a patient history on the outcome that the score is intended to predict. The combination of these effects can occur in multiple ways using the set of weights 120 and sets of events extracted from a patient history.

In the following example implementation, the sets of events are categorized in multiple categories. For example: procedures, diagnoses, primary diagnoses, chronic conditions, one-time events, medications including dosage, lab results, imaging results, etc. For each patient, the computer system constructs, as the set of events, a plurality of timelines 140 of events based on such categorization. Examples of kinds of timelines that can be constructed include but are not limited to: a history of all events; a history of all events occurring during inpatient hospitalizations; a history of all diagnoses; a history of all principal procedures; a history of all medications; a history of all lab results; a history of all imaging results; and so on. A timeline of events 140 is thus a set of events from the patient history for a selected one or more categories or types of events. In some timelines, all of the events of a selected type may be used. In some timelines, a selection of events may be used. For example, for a medication that is taken over a long time, or for a diagnosis of a chronic condition, a timeline may be generated for all events, and another timeline may be generated that includes only a first event, or a change between events, or other form of selection of the events.

A timeline generator module 142 can be implemented as computer program code processed by a processing system of a computer system, such as a general-purpose computer as shown in FIG. 4. The timeline generator module creates data structures in memory representing timelines 140.

For each timeline of a patient, the computer system computes a corresponding function of the weights of the events included in each timeline 140 for the patient to provide quantities 150. One example function is a weighted sum. Another example function is a maximum among all the weights of the timeline. A quantity 150 is a result of an operation that involves one of the set of weights 120 and one timeline 140. Although FIGS. 1A, 1C, and 1D show N timelines and N quantities, there can be multiple quantities 150 computed for each timeline 140.

As noted above, there can be one or more sets of weights. In general, a set of weights is generated for each type of outcome to be predicted, estimated or inferred by the predictive model. For example, there can be a set of weights for predicting future utilization, mortality and re-admission. A different set of weights is used for each different outcome to be processed. In some implementations, multiple sets of weights can be used and applied to generate inputs to the predictive model.

Thus, as an example, the set of weights 120 for future resource utilization and a timeline 140 for all events for the patient can be used to generate one quantity 150 for the patient. The set of weights 120 for future medication cost and a timeline 140 of medication events and/or procedure events can be used to generate another quantity 150 for the patient.

To compute the quantity 150 for a patient's timeline using the specific set of weights for that type of timeline, the following steps are performed. For each event in that type of timeline of the patient, the relative time of the event and any entity profile characteristics, such as age, comorbidity(ies), and behaviors of the patient, are computed or retrieved from the data for the patient. The computation of the relative time can be based on a selected input time 154. Such computation may occur on demand or may have been performed in a periodic batch job. This set of data for that event is used to lookup a weight for that event from the specified set(s) of weights. A calculator module 152 can be implemented as computer program code processed by the processing system of a computer, such as in FIG. 4, to perform this computation of the relative times and quantities 150 from the input timeline data 140 and the set of weights 120.

As a result of applying this process to a given patient, or a set of patients, each patient is now characterized by the plurality of quantities 150 as generated for the plurality of timeline types. This computation can be performed for data records for one or more selected patients from the data storage 102 for whom a trained predictive model will be applied, as indicated at 130 (See FIGS. 1A and 1D), or for a training set 132 of data that is used to train the predictive model 104 (See FIGS. 1A and 1C). The quantities 150 computed for the timelines for a given entity are the input to a predictive model, which outputs a value indicative of an outcome for that entity, whether applying a trained predictive model (FIG. 1D), or during training of the predictive model (FIG. 1C). The predictive model also can receive, as input features, any other patient data, whether from a training set (136) or other entity data (130), such as demographic data or medical data.

In the training processes described above, the set of weights 120 and the predictive model 104 are trained using data sets for entities for which the outcome is known, where the output of the predictive model otherwise would predict, estimate, or infer the outcome. The training set 132 for training the predictive model and training set 124 for training the set of weights can be different sets of data records to reduce the risk of overfitting the predictive model. The training sets 124 and 132 can be stored in the data storage 102 or may be received by the computer system from another source.

During training of the predictive model, the data from training set 132 which is relevant to computing timelines, as indicated at 134, is processed by the timeline generation module. The data from those data records that includes the known outcomes as well as any other entity data used as input features for the predictive model, such as demographic and medical data, as indicated at 136, for the purposes of training the predictive model, are paired up with the quantities 150 generated for those records to create the training set 160 used by the predictive model training module 108 to train the predictive model 104.

The quantities 150 for the plurality of timelines 140 which are computed for an entity form a set of predictive features that are inputs to a predictive model. The predictive model outputs a score based on the combined set of predictive features, from which an outcome, present or future, can be inferred. The predictive model can be any time of model, such as a machine learning, deep learning or Bayesian module, or other predictive modeling algorithm. The predictive model can be linear or non-linear. As further examples, the predictive model can be a classifier, a regressor, a clusterer or other algorithm that can be used to estimate outcomes in the future or outcomes in the present which are not directly measurable from the data in the data storage 102. Classifiers or clusterers are used to predict an outcome with a set of discrete outcomes, whereas regressors are used to predict a continuous outcome. The quantities 150 for a plurality of event timelines 140 can be computed for a patient, or for a set of patients, on a periodic basis, e.g., monthly. This data can be used to create predictive models using time-series algorithms including deep neural network methods such as recurrent neural networks.

As noted above, the predictive model produces a score 106. In some implementations, the score can be a continuous predicted/estimated output of a regressor. In some implementations the score can be a probability of a certain class of a classifier. In some implementations, the score can represent a value from a set of discrete values. In some implementations, the score can represent a value from a range of continuous values. The score can be in a variety of forms depending on the nature of the predictive model. Example ways in which a score can be presented include, but are not limited to, a rank, a percentile, a category, presence in a range, a cost, a risk, or an amount, or other value depending on the outcome to be represented using the score.

The score can be mapped onto a specific scale, for example a 1-1000 scale. Making the score available to end users in such a scale enjoys the benefit of an easy mental map between score and risk which can help produce material to guide end users on using the score. For example, literature may specify to the end-user levels of severity associated with score ranges. For example: Scores from 800-1000 are the highest expected future cost patients with a specified average expected future cost. Furthermore, a scale such as 1-1000 makes it easier for end users to form their own mental patterns associating the score with quick understanding of the patient risk level, after the end user has used the score for a period of time. The standardized scale (e.g., 1-1000) also allows easy benchmarking which in turn allows even faster and better end-user familiarity with score values and corresponding risk of a patient. This results in enhanced usability. Using a standardized scale also allows entities to be ranked and/or categorized using the score. Also, when there are two different outcomes which are correlated, the predictive model can generate a value indicative of a first outcome for an entity, and then the computer system can report a value indicative of the second outcome for the entity based on the value indicative of the first outcome for the entity. For example, a ranking or categorization using scores for one outcome can be used to map entities to corresponding rankings or categorizations for another, correlated outcome. As another example, the computer system can include a mapping of scores from a range of continuous values for the first outcome to scores indicative of the second outcome.

Figure 3:
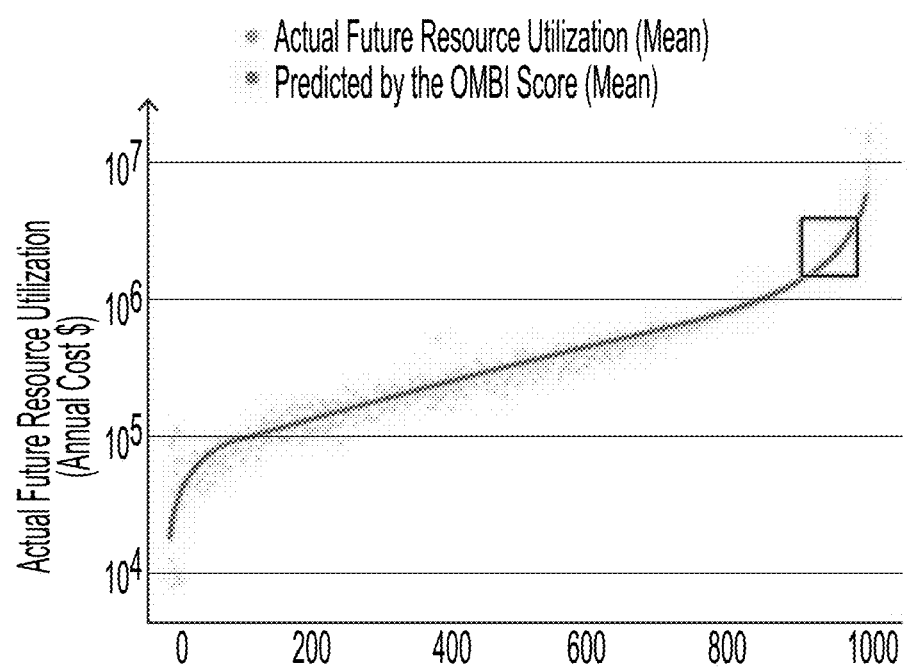
FIG. 3 is an illustrative example of a graph relating the output of a predictive model with known outcome data.

FIG. 3 is a graphical representation of an illustrative example of a relationship between scores produced by the predictive model 104 and how they correlated to actual outcomes, which in this is example actual costs. In this example the score has been mapped to a scale of 1-1000. In this graphical representation, the x-axis represents scores output by the predictive model; the y-axis represents actual resource utilization occurred at a future time. In some implementations, the score output by the predictive model can be presented graphically by a position along a graphical element representing a range of possible values. The score output by the predictive model also can be illustrated with respect to a baseline or previous score to allow comparisons.

The scores output by a predictive model can represent an evaluation of outcome risks. The risk is driven by patient event history (condition, procedure, medications, lab results, etc.). To provide transparency into the underlying patient events that contribute the most to the patient outcome risk, the system can include a data structure with data representing a mapping of features input to the predictive model to other features in the data set that help to explain the output of the model, in terms of what data in the patient event history had an impact on the outcome of the model. This data structure can identify the data that correspond to actionable or medically modifiable factors, which includes a set of factors that can be acted upon by the user of the predictive model. These factors can be a subset of the factors that explain the output of the predictive model. This analysis is personalized to a particular patient. As described in U.S. patent application Ser. No. 15/927,766, entitled "Information System Providing Explanation of Models", filed Mar. 21, 2018, incorporated by reference, the computer system builds a "personalized" model with respect to the selected entity, based on a trained predictive model, by using data values for the selected entity to fix certain inputs to the predictive model. The computer system inputs one or more different data values for selected input features of the personalized model, while data values for the remaining input features of the personalized model are fixed to data values for the selected entity.

The foregoing description is an example implementation of a computer system implementing a health care information system. The various computers used in this computer system can be implemented using one or more general-purpose computers, such as client computers, server computers and database computers, which can be programmed to implement the functionality such as described in the example implementation.

As noted above, in an example implementation such processing can be performed by a big data processing system, which processes in pipeline fashion, input medical histories of the patients of interest, in the form of data representing diagnoses, procedures and medications. These inputs can be any collection of data fields storing values for data. The pipeline computes the corresponding function of weights and timelines for each patient, distributing these calculations among a cluster of server computers implementing a scalable data processing engine, such as the Apache SPARK engine. This data processing engine facilitates the processing of medical histories in a batch (for example, an overnight run for that day's patients) or as a stream (for example, updating a patient's record in real time after a change in their medical history). The computer system converts the data into one or more timelines for each patient, applies a function to the weights and timelines to generate the quantities to input to the predictive model, and then applies the predictive model to the quantities to provide the output scores for each patient. These scores can be saved, for example to storage as a partitioned data file, to facilitate insertion of the outcomes scores into the corresponding database in the data storage 102.

Given the output of the predictive model 104 for a given patient, and with such outputs for multiple patients stored as part of the patient data in data storage 102, the computer system can provide, to health care providers, information about these predicted outcomes in the form of communications and reports which identify patients who are at risk and which provide information explaining that risk, such as risk factors.

Figure 5:
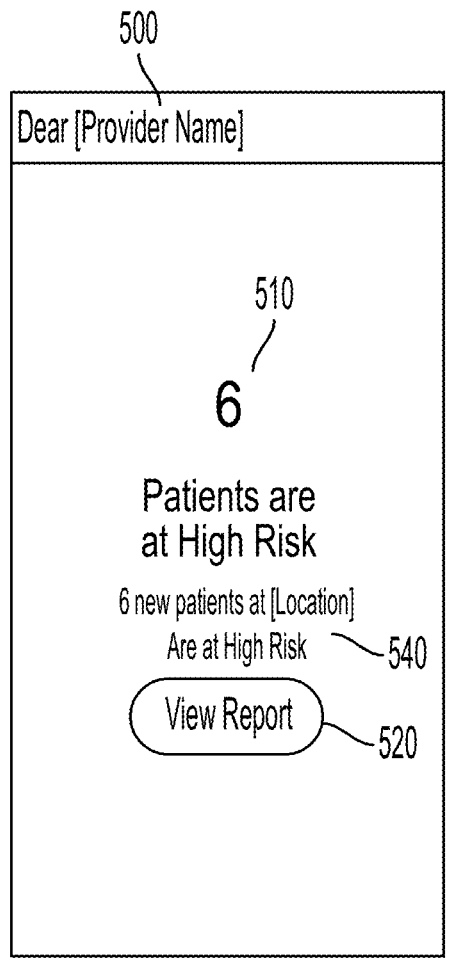
FIG. 5 is an example graphical user interface for a mobile device accessing the computer system.

An example graphical user interface for an application on a mobile device is shown in FIG. 5. This application can be implemented as computer program code processed by a processing system of a mobile device, the mobile device being a kind of computer as shown in FIG. 4. The mobile device has authorized, secure access to the computer system 100, which generally allows access by a provider who has logged into the computer system 100 and has been authenticated and verified. A health care provider typically has a name, which can be shown in the interface (e.g., at "[Provider Name]" 500), and typically is associated with a health care facility, which can be shown in the interface (e.g., at "[Location]" 540). Patients generally are associated with a health care provider and/or a health care facility. The computer system identifies those patients associated with a provider and identifies those patients for that provider who have an elevated risk based on the predicted outcomes from the model 104. Information about these patients can be formatted into a report, and information summarizing these patients can be sent to the provider on a mobile device. For example, a provider may receive a notification that a number of patients is at high risk, as indicated at 510. The number of patients also can be limited to those patients with a specified condition, and an indication of this condition also can be included as part of the notification. The application on the mobile device may provide a way for the provider to initiate access to a more detailed report for these patients, as indicted by the button 520. In response to the provide manipulating the button 520, the application sends a request to the computer system to access the more detailed report.

FIG. 6 is an illustrative example of a graphical user interface that provides a more detailed report for one or more patients. This interface provides a row for each patient, and several columns of information. In this example, the columns include a patient identifier 600, a date 602 of a relevant procedure or other event, a date 604 an alert was generated by the system, an optional representation of a score 606 based on the output by the predictive model 104, and indications 608 of any risk factors this patient has. In this example, the score is shown as a linear meter for a value in the range of 1-1000. The score can be in any of a variety of ranges, and any graphical illustration, such as a meter or dial, can reflect the range of the score and where the patient's score falls on that range. The score may be presented merely as a number, or other alphanumeric value on a known scale, without a graphical representation of the range for the score.

FIG. 4 is a block diagram of a general-purpose computer which processes computer program code using a processing system. Computer programs on a general-purpose computer generally include an operating system and applications. The operating system is a computer program running on the computer that manages access to various resources of the computer by the applications and the operating system. The various resources generally include memory, storage, communication interfaces, input devices and output devices.

Examples of such general-purpose computers include, but are not limited to, larger computer systems such as server computers, database computers, desktop computers, laptop and notebook computers, as well as mobile or handheld computing devices, such as a tablet computer, hand held computer, smart phone, media player, personal data assistant, audio and/or video recorder, or wearable computing device.

With reference to FIG. 4, an example computer 400 comprises a processing system including at least one processing unit 402 and a memory 404. The computer can have multiple processing units 402 and multiple devices implementing the memory 404. A processing unit 402 can include one or more processing cores (not shown) that operate independently of each other. Additional co-processing units, such as graphics processing unit 420, also can be present in the computer. The memory 404 may include volatile devices (such as dynamic random access memory (DRAM) or other random access memory device), and non-volatile devices (such as a read-only memory, flash memory, and the like) or some combination of the two, and optionally including any memory available in a processing device. Other memory such as dedicated memory or registers also can reside in a processing unit. This configuration of memory is illustrated in FIG. 4 by dashed line 404. The computer 400 may include additional storage (removable and/or non-removable) including, but not limited to, magnetically-recorded or optically-recorded disks or tape. Such additional storage is illustrated in FIG. 4 by removable storage 408 and non-removable storage 410. The various components in FIG. 4 are generally interconnected by an interconnection mechanism, such as one or more buses 430.

A computer storage medium is any medium in which data can be stored in and retrieved from addressable physical storage locations by the computer. Computer storage media includes volatile and nonvolatile memory devices, and removable and non-removable storage devices. Memory 404, removable storage 408 and non-removable storage 410 are all examples of computer storage media. Some examples of computer storage media are RAM, ROM, EEPROM, flash memory or other memory technology, CD-ROM, digital versatile disks (DVD) or other optically or magneto-optically recorded storage device, magnetic cassettes, magnetic tape, magnetic disk storage or other magnetic storage devices. Computer storage media and communication media are mutually exclusive categories of media.

The computer 400 may also include communications connection(s) 412 that allow the computer to communicate with other devices over a communication medium. Communication media typically transmit computer program code, data structures, program modules or other data over a wired or wireless substance by propagating a modulated data signal such as a carrier wave or other transport mechanism over the substance. The term "modulated data signal" means a signal that has one or more of its characteristics set or changed in such a manner as to encode information in the signal, thereby changing the configuration or state of the receiving device of the signal. By way of example, and not limitation, communication media includes wired media such as a wired network or direct-wired connection, and wireless media include any non-wired communication media that allows propagation of signals, such as acoustic, electromagnetic, electrical, optical, infrared, radio frequency and other signals. Communications connections 412 are devices, such as a network interface or radio transmitter, that interface with the communication media to transmit data over and receive data from signals propagated through communication media.

The communications connections can include one or more radio transmitters for telephonic communications over cellular telephone networks, and/or a wireless communication interface for wireless connection to a computer network. For example, a cellular connection, a Wi-Fi connection, a Bluetooth connection, and other connections may be present in the computer. Such connections support communication with other devices, such as to support voice or data communications.

The computer 400 may have various input device(s) 414 such as a various pointer (whether single pointer or multi-pointer) devices, such as a mouse, tablet and pen, touchpad and other touch-based input devices, stylus, image input devices, such as still and motion cameras, audio input devices, such as a microphone. The compute may have various output device(s) 416 such as a display, speakers, printers, and so on, also may be included. All of these devices are well known in the art and need not be discussed at length here.

The various storage 410, communication connections 412, output devices 416 and input devices 414 can be integrated within a housing of the computer, or can be connected through various input/output interface devices on the computer, in which case the reference numbers 410, 412, 414 and 416 can indicate either the interface for connection to a device or the device itself as the case may be.

An operating system of the computer typically includes computer programs, commonly called drivers, which manage access to the various storage 410, communication connections 412, output devices 416 and input devices 414. Such access generally includes managing inputs from and outputs to these devices. In the case of communication connections, the operating system also may include one or more computer programs for implementing communication protocols used to communicate information between computers and devices through the communication connections 412.

Any of the foregoing aspects may be embodied as a computer system, as any individual component of such a computer system, as a process performed by such a computer system or any individual component of such a computer system, or as an article of manufacture including computer storage in which computer program code is stored and which, when processed by the processing system(s) of one or more computers, configures the processing system(s) of the one or more computers to provide such a computer system or individual component of such a computer system.

Each component (which also may be called a "module" or "engine" or the like), of a computer system such as described herein, and which operates on one or more computers, can be implemented as computer program code processed by the processing system(s) of one or more computers. Computer program code includes computer-executable instructions and/or computer-interpreted instructions, such as program modules, which instructions are processed by a processing system of a computer. Generally, such instructions define routines, programs, objects, components, data structures, and so on, that, when processed by a processing system, instruct the processing system to perform operations on data or configure the processor or computer to implement various components or data structures in computer storage. A data structure is defined in a computer program and specifies how data is organized in computer storage, such as in a memory device or a storage device, so that the data can accessed, manipulated and stored by a processing system of a computer.

It should be understood that the subject matter defined in the appended claims is not necessarily limited to the specific implementations described above. The specific implementations described above are disclosed as examples only.

What is claimed is:

1. A computer system, comprising:
    a processing system comprising a processing device and computer storage medium;
    a predictive model comprising computer program code stored in the computer storage medium and processed by the processing system and having an input that receives data values for input features derived from event data from historical data for an entity and an output that provides data representing a result from the predictive model processing the received data values for the input features, wherein the result comprises a value indicative of a predicted outcome for the entity relative to an input reference time;
    a timeline generation module comprising computer program code stored in the computer storage medium and processed by the processing system and having an input to receive event data from historical data for an entity, and an output that provides a plurality of timelines for the entity, each timeline comprising data representing a respective set of events from the received event data;
    a set of weights stored in the computer storage wherein the set of weights comprises a respective distinct weight for each tuple in a plurality of tuples, each tuple representing a respective distinct combination of at least a type of event, a respective relative time of the event with respect to a reference time, and one or more entity profile characteristics for an entity;
    a calculation module comprising computer program code stored in the computer storage medium and processed by the processing system and having a first input that receives the plurality of timelines provided by the timeline generation module for the entity and a second input that receives the input reference time, the calculation module:
    for each timeline, accessing, from the set of weights in the computer storage, a respective weight for each event in the timeline, based on the type of the event, the respective relative time of the event with respect to the input reference time, and one or more entity profile characteristics of the entity, and
    for each timeline, computing a respective additional feature for the entity as a respective function of the retrieved respective weights for each event in the timeline; and
    wherein the predictive model receives, as the input features, at least the data values derived from the event data for the set of events from the historical data for the entity and the respective additional features computed for the timelines for the entity computed by the calculation module, and wherein the predictive model computes the predicted outcome for the entity relative to the input reference time based on both the data values for the features derived from the event data from the historical data for the entity and the additional features computed for the timelines for the entity.

2. The computer system of claim 1, wherein the input reference time comprises a current time.

3. The computer system of claim 1, wherein the input reference time comprises a time associated with an event.

4. The computer system of claim 1, wherein the input reference time comprises a time for which the outcome of the predicted model is computed.

5. The computer system of claim 1, wherein the respective function for a timeline among the plurality of timelines is different from the respective function for at least one other timeline among the plurality of timelines.

6. The computer system of claim 1, wherein the function comprises a linear function.

7. The computer system of claim 1, wherein the function comprises a non-linear function.

8. The computer system of claim 1, wherein each unique tuple in the set of weights has a single weight.

9. The computer system of claim 1, wherein at least one tuple in the set of weights comprises a plurality of weights, and the calculation module selects from among the plurality of weights.

10. The computer system of claim 1, wherein the historical data for entities comprises patient medical histories, and wherein the entity comprises a patient, and the entity profile characteristic comprises at least one of age, a comorbidity, a behavior, a characteristic from a family history, or genetic profile attribute of the patient, and wherein categories of events include at least one of a medical diagnosis, a medical procedure, a medical treatment, a medical laboratory result, or a medication prescribed or purchased or administered for a patient, and wherein types of events correspond to one or more event codes or one or more medical instances.

11. The computer system of claim 1, wherein the set of weights comprises a plurality of weight tables, including a first weight table for a first outcome and a second weight table for a second outcome different from the first outcome, wherein a first predictive model generates values indicative of the first outcome using the first weight table, and a second predictive model generates values indicative of the second outcome using the second weight table.

12. The computer system of claim 1, wherein the set of weights comprises a weight table corresponding to a first outcome, and wherein the predictive model outputs a value indicative of a second outcome different from the first outcome.

13. The computer system of claim 12, wherein the second outcome is correlated with the first outcome.

14. The computer system of claim 1, wherein the set of weights comprises a plurality of weight tables, wherein the calculation module accesses the plurality of weight tables to compute the results provided as inputs to the predictive model.

15. The computer system of claim 1, wherein the predictive model generates a value indicative of a first outcome for an entity, wherein the first outcome is correlated to a second outcome, and the computer system reports a value indicative of the second outcome for the entity based on the value indicative of the first outcome for the entity.

16. The computer system of claim 10, wherein a plurality of types of events are grouped together as a medical instance, and wherein at least one weight in the set of weights is associated with the medical instance.

17. The computer system of claim 10, wherein the plurality of categories of events include at least two of procedures codes, medication codes, or diagnosis codes.

18. The computer system of claim 1, wherein the set of weights comprises a plurality of different weights for a type of event for different combinations of that type of event with different relative times.

19. The computer system of claim 1, wherein for a first tuple having a first weight for a first combination of a first type of event and a first relative time, and a second tuple having a second weight for a second combination of the first type of event and a second relative time longer than the first relative time, the first weight is less than the second weight.

20. The computer system of claim 19, wherein for a third tuple having a third weight for a third combination of a second type of event and a third relative time, and a fourth tuple having a fourth weight for a fourth combination of the second type of event and a fourth relative time longer than the third relative time, the third weight is greater than the fourth weight.

21. The computer system of claim 1, wherein the result output for an entity by the predictive model comprises a value indicative of a probability the entity has the outcome.

22. The computer system of claim 1, wherein the result output for an entity by the predictive model comprises a value from a set of discrete values.

23. The computer system of claim 22, wherein the discrete range of values comprises a finite set of integers comprising at least 1 to 1000.

24. The computer system of claim 1, wherein the result output for an entity by the predictive model comprises a value from a range of continuous values.

25. The computer system of claim 1, wherein the result output for an entity by the predictive model comprises a value from a scale that ranks or categorizes entities with respect to the outcome.

26. The computer system of claim 25, wherein the scale comprises a finite set of integers comprising at least 1 to 1000.

27. The computer system of claim 1, wherein the result output for an entity by the predictive model comprises a value indicative of a probability the entity has the outcome.

28. The computer system of claim 1, wherein the result output for an entity by the predictive model comprises a value indicative of an estimation of risk that the entity has the outcome.

29. The computer system of claim 1, further comprising a timeline generation module converting event data for an entity into a timeline, and wherein the calculation module computes a function of the weights from the set of weights and event data in the timeline to generate an input for the predictive model.

30. The computer system of claim 1, wherein the relative time for events in the set of weights is computed in units of months.

* * * * *